(12) United States Patent
Jasperse

(10) Patent No.: US 12,298,233 B2
(45) Date of Patent: May 13, 2025

(54) METHOD AND ANALYZER TO CORRECT FOR UNKNOWN INTERFERENCES IN A PATIENT BLOOD SAMPLE

(71) Applicant: Siemens Healthcare Diagnostics Inc., Tarrytown, NY (US)

(72) Inventor: Jeffrey R. Jasperse, Newton, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 222 days.

(21) Appl. No.: 18/000,938

(22) PCT Filed: Jun. 9, 2021

(86) PCT No.: PCT/US2021/036515
§ 371 (c)(1),
(2) Date: Dec. 7, 2022

(87) PCT Pub. No.: WO2021/252564
PCT Pub. Date: Dec. 16, 2021

(65) Prior Publication Data
US 2023/0221244 A1    Jul. 13, 2023

Related U.S. Application Data

(60) Provisional application No. 63/037,767, filed on Jun. 11, 2020.

(51) Int. Cl.
*G01N 21/31* (2006.01)
*G01N 1/40* (2006.01)
(Continued)

(52) U.S. Cl.
CPC .......... *G01N 21/31* (2013.01); *G01N 1/4077* (2013.01); *G01N 33/491* (2013.01); *G01N 33/721* (2013.01); *G01N 2015/011* (2024.01)

(58) Field of Classification Search
CPC . G01N 33/721; G01N 21/31; G01N 2015/011
See application file for complete search history.

(56) References Cited

U.S. PATENT DOCUMENTS 9,097,701 B2    8/2015  Krogh
2003/0027347 A1    2/2003  Shapiro
(Continued)

FOREIGN PATENT DOCUMENTS

KR    101597310 B1 *    2/2016
WO    WO-2011019576 A1 *    2/2011    ........... G01F 23/292
(Continued)

OTHER PUBLICATIONS

Vikram Surendran, "Acoustofluidic Micromixing Enabled Hybrid Integrated Colorimetric Sensing, for Rapid Point-of-Care Measurement of Salivary Potassium" May 28, 2019 (Year: 2019).*
(Continued)

*Primary Examiner* — Maurice C Smith

(57) ABSTRACT

Analyzers and methods of use are disclosed, including a blood analyzer comprising a light source to transmit an optical signal; a detector to generate data indicative of optical signal intensity; a transparent sample vessel between the light source and the detector; a dispensing device to pass a first portion of the blood sample comprising whole blood or lysed blood into the vessel at a first instance of time, and to pass a plasma portion of the blood sample into the vessel at a second instance of time; a controller to cause a processor to obtain first and second data generated by the detector, the first data indicative of the optical signal passing through the first portion of the blood sample and the second data indicative of the optical signal passing through the plasma, to determine a total absorbance spectrum in which the first data is adjusted by the second data.

17 Claims, 6 Drawing Sheets

(51) Int. Cl.
  *G01N 33/49* (2006.01)
  *G01N 33/72* (2006.01)
  *G01N 15/01* (2024.01)

(56) References Cited

U.S. PATENT DOCUMENTS

| | | |
|---|---|---|
| 2004/0166031 A1 | 8/2004 | Taylor et al. |
| 2005/0036147 A1 | 2/2005 | Sterling et al. |
| 2008/0112853 A1 | 5/2008 | Hall |
| 2010/0105020 A1* | 4/2010 | Schmidt ............... G01N 33/723 435/2 |
| 2010/0150779 A1 | 6/2010 | Chow et al. |
| 2012/0149126 A1 | 6/2012 | Wilson et al. |
| 2018/0037883 A1 | 2/2018 | Laugharn, Jr. et al. |

FOREIGN PATENT DOCUMENTS

| | | | |
|---|---|---|---|
| WO | 2018017199 A1 | 1/2018 | |
| WO | WO-2018034343 A1 * | 2/2018 | ......... G01B 9/02025 |
| WO | 2019213484 A1 | 11/2019 | |
| WO | 2021222084 A1 | 11/2021 | |

OTHER PUBLICATIONS

International Search Report and Written Opinion of International Application No. PCT/US2021/036515 dated Sep. 28, 2021.
Dawson et al., "Direct Determination of Zinc in Whole Blood, Plasma and Urine By Atomic Absorption Spectroscopy"; Clinica Chimica Acta, Elsevier BV; vol. 26; No. 3; published: May 1, 1969; pp. 465-475.

* cited by examiner

METHOD AND ANALYZER TO CORRECT FOR UNKNOWN INTERFERENCES IN A PATIENT BLOOD SAMPLE

This application claims benefit under 35 USC § 119(e) of U.S. Provisional Application No. 63/037,767, filed Jun. 11, 2020. The entire contents of the above-referenced patent application(s) are hereby expressly incorporated herein by reference.

TECHNICAL FIELD

The present disclosure relates to an improved method and sample analyzer that corrects for unknown extracellular interferents, such as in blood samples, without advanced knowledge of a spectral profile signature of the extracellular interferent.

BACKGROUND

Various types of tests related to patient diagnosis and therapy can be performed by analysis of a sample, such as a patient's bodily fluids. These tests typically use automated sample analyzers onto which vials (for example, cuvettes, syringes, vacutainers, capillary tubes, etc.) containing samples have been loaded. The sample analyzer extracts the samples from the vials and combines the samples with various reagents in reaction vessels. Frequently, the samples are incubated or otherwise processed before being analyzed. Such sample analyzers obtain measurements from the sample in order to determine the presence and/or amount of analyte of interest. Although various known clinical analyzers for chemical, immunochemical and biological testing of samples are available, analytical clinical technology is challenged by increasing needs for improved levels of analysis. The improvement of analytical sensitivity continues to be a challenge.

Typical sample analyzers use an optical system during the test procedure to obtain readings from the sample. A typical optical system has an aligned light source and a detector (e.g., spectrophotometer). The sample vessel contains the sample and a reagent and is positioned between the light source and detector along an optical axis centerline of the light source. The light source emits broadband light into the input region into the sample-reagent combination inside the vessel. A chemical reaction of the sample-reagent combination produces chromophores absorbing light at specific wavelengths proportional to the concentration of the analyte being measured. Light emitted from the illuminated sample-reagent combination inside the vessel exits the output region and is detected by the detector.

The detector obtains an absorbance measurement of the emitted light signal at specific wavelengths following the Beer-Lambert law: Absorbance=$-\log_{10}(\%T/\%T_0)$, where T is the transmission of light through the sample of interest in the vessel, and $T_0$ is the transmission of light through a spectrally inert solution often referred to as the "blank" term. In addition to absorbance readings, other readings may be obtained, such as turbidimetric, fluorometric, and like readings. The obtained readings are used to determine the concentration of one or more analytes in the sample using well-known calibration techniques.

Whole blood is the natural state of blood consisting of virtually transparent plasma within which red blood cells are suspended (that contain the absorbing pigment, hemoglobin, of interest), lipids, white blood cells, platelets, and a host of other constituents. Several considerations must therefore be addressed in order to design an instrument that will provide an accurate measure of the hemoglobin content.

One consideration is light scatter that traditionally has been minimized by breaking the red blood cells to form a homogenous mixture with the plasma called lysed blood. Some devices lyse the red blood cells using ultrasound. Some point-of-care testing devices use spectrophotometric optical absorption measurement for the determination of the oximetry parameters on a whole blood sample. These devices are fluidic systems that typically position the patient blood sample in a slide cell sample chamber for testing the blood sample. For example, one system described in U.S. Pat. No. 9,097,701 ("Apparatus for Hemolyzing a Blood Sample and for Measuring at Least One Parameter Thereof", issued Aug. 4, 2015) uses two piezo elements, with two balanced resonant elements, surrounding a sample chamber symmetrically, to lyse the red blood cells using acoustophoretic forces. However, these devices are difficult and expensive to manufacture, including requiring a highly precise symmetry with specially made resonant elements.

Improved lysis devices and methods, which may also be used for plasma separation, are described in the provisional application entitled "ACOUSTOPHORETIC LYSIS DEVICES AND METHODS", application Ser. No. 63/036,537, filed on Apr. 28, 2020, which is hereby incorporated in its entirety herein.

While scatter is not completely eliminated with lysed blood approaches (lipids, cell debris, and other large particles are still present), the nonlinearities induced by the residual scatter are small enough to be neglected or treated with simple corrections to account for their effects.

Other considerations are the sample vessel dimensions and optical design to ensure that the measurement takes place within an optimal absorption spectrum (adequate signal to noise) and at a fixed, known path length of the apparatus, respectively. Absorption can be adjusted by known dilution of the blood or by appropriate choice of sample vessel dimensions (for example, path length). The optical design may ensure that the incident source light is adequately collimated to create a unique path length and that enough transmitted light is collected to satisfy signal strength requirements.

Human blood, in particular, is composed of cellular components and plasma. The cellular components are red blood cells (RBC), white blood cells (WBC) and platelets comprising about 45% of the total volume. The remaining plasma components comprise about 55%, of which water is about 90%, and the solids are about 10% (ionic components Na+, K, Mg+2, Cl—, etc., and organic components lipids, glucose, vitamins, hormones, amino acids, urea, drug therapies, etc.). The proportion of cells to plasma is not always 55% to 45%, the proportion is dependent on a patient's physiological condition. This has been thoroughly studied and reported over decades and is approximately 45% to 52% for men, 37% to 48% for women.

A patient blood sample's total hemoglobin tHb is of particular interest in determining a patient's physiological health. Total hemoglobin concentration is presented as g/dL. Total hemoglobin tHb is the sum of the constituent fraction concentrations contained in the red blood cells: Oxyhemoglobin $O_2Hb$, Deoxyhemoglobin HHb, Carboxyhemoglobin COHb and Methemoglobin MetHb. These constituent concentrations are of particular interest and known as hemoglobin forms. The measurement method for the hemoglobin forms is known in the industry as Oximetry, or CO-Oximetry which may be referred to herein as "Coox".

Each of these hemoglobin forms has a unique spectral profile signature, in the wavelength range of 450 nm to 680 nm. These spectral profile signatures coefficients are generated by measuring carefully formulated reference samples, applying a rigorous process and statistics using high resolution laboratory equipment. In general, spectral profiles may be quantified as numbers with the following processes: spectrometers deploy a linear photodiode array having N number of pixels, and a diffraction grating that separates out N discrete wavelengths within the wavelength range; each pixel receives light from the grating at a single dominant wavelength, and produces an electrical charge signal proportional to the amount of incident light at this wavelength; and, each pixel signal is digitized by an analog to digital converter. Hence a spectral profile contains N wavelength values. Higher wavelength resolution is achieved by interpolating between pixels resulting in more than N wavelengths.

There are specific constituents contained in the red blood cells (intracellular), and specific constituents contained in the blood plasma (extracellular) that are not of interest in determining the hemoglobin forms (discussed below). In general, conventional blood gas Co-Oximeter analyzers obtain a total absorbance measurement for a lysed blood sample over the wavelength range of 450 nm to 680 nm by measuring the transmittance through the lysed blood sample (% TspecimenLysedBlood), and measuring the transmittance through a clear solution such as deionized water or clear calibration solution (% TblankCAL); and then calculating the total absorbance using the following formula:

$$CooxAbsorbance = -\log10\left(\frac{\% \; TspecimenLysedBlood}{\% \; TblankCAL}\right)$$

Then, a known "extinction coefficient" for each hemoglobin form or other analyte of interest is mathematically applied to the total Coox Absorbance measurement to determine a concentration for each hemoglobin form (or other analyte of interest) from the total absorbance measurement. An exemplary formula for calculating the spectral coefficient vector of dimension $\lambda_i$ to determine a hemoglobin form concentration is set forth below:

Absorbance($\lambda_i$)=AnalyteConcentration($\lambda_i$)*ExtictionCoefficient($\lambda_i$)*pathlength where Absorbance($\lambda_1$) is the absorption at discrete wavelength $\lambda_i$, AnalyteConcentration($\lambda_i$) is the analyte concentration to be determined at $\lambda_i$, ExtinctionCoefficient($\lambda_i$) is the known absorbance at $\lambda_i$ of the specific analyte of interest, and pathlength is the thickness of the sample vessel containing the blood sample (a constant).

Specific constituents, however, that are not of interest within the lysed blood sample, or other sample, are referred to in the art as "interferents" or "interfering substances". These interfering substances cause errors in the calculated concentrations of the hemoglobin forms, and must be detected and corrected for. There are two types of interferents, i.e., intracellular interferents and extracellular interferents. Intracellular interferents originate from the red blood cells. Extracellular interferents originate from the plasma. Commonly known extracellular interferents include: lipids, methylene dies used in cyanosis therapy, and hydroxocobalamin used in vitamin $B_{12}$ therapy. With respect to known interfering substances, each has a unique spectral profile within the 450 nm to 680 nm range where the hemoglobin forms of interest are measured. The spectral profiles of the known interfering substances are measured and programmed into the blood gas analyzers so that the blood gas analyzers can recognize and correct for the known interfering substances.

Unknown interferents, however, can occur unexpectedly in blood samples, such as when new drug therapies are introduced. In prior art systems, when unknown interferents are detected, the analyzer result accuracy may be compromised and marked as not useable. Often a field notice is issued. This problem often requires the manufacturer of the analyzer to take corrective action, conduct sample studies, conduct verification and validation studies, and then issue a software release to include the spectral signature of the newly detected interferant.

It is desirable to produce a blood gas analyzer that corrects for new and unknown interferents without requiring field notices, sample studies, verification studies, validation studies and new software releases. The present disclosure is directed to an improved blood gas analyzer method that corrects for unknown extracellular interferents without advanced knowledge of the spectral profile signature of the unknown extracellular interferent and by measuring the samples in real time without requiring mathematical correction for the unknown extracellular interferents.

SUMMARY

The problem of measuring absorbance in samples having unknown interferences is addressed through analyzers and methods of use of analyzers to determine and account for unknown interferences in the samples utilizing absorbance and/or transmittance measurements from a detector.

In one aspect of the disclosure, a blood analyzer may comprise a housing assembly that defines an internal space; a light source mounted to the housing assembly in the internal space, the light source configured to generate an optical signal having wavelengths spanning a range from 450 nm to 680 nm, the optical signal being transmitted through a path; a detector within the path of the optical signal, the detector configured to generate data indicative of intensity of the optical signal at wavelengths within the range; a transparent sample vessel positioned within the path between the light source and the detector such that the optical signal passes through the transparent sample vessel prior to being received by the detector; a dispensing device adapted to pass a first portion of the blood sample into the transparent sample vessel at a first instance of time, the first portion being whole blood or lysed blood, and to pass the plasma sample into the sample vessel at a second instance of time; a controller having a processor executing logic that when executed by the processor causes the processor to obtain first data generated by the detector indicative of the optical signal passing through the first portion of the blood sample, and second data generated by the detector indicative of the optical signal passing through a plasma sample, the logic causing the processor to calculate a total absorbance spectrum in which the first data is adjusted by the second data.

In one aspect of the present disclosure, the analyzer may comprise a plasma separator to separate plasma from a blood sample to create a plasma sample. In one aspect of the present disclosure, the analyzer may comprise a lysis device, and the first portion of the blood sample may be lysed with the lysis device.

In one aspect of the present disclosure, the first data may have first values indicative of the absorbance of the first portion of the blood sample at various wavelengths, and the second data may have second values indicative of absorbance of the plasma sample at various wavelengths, and wherein the first data is divided by the second data.

In one aspect of the present disclosure, a computerized method may be performed by a processor executing computer executable code stored on a computer readable medium, comprising: actuating a plasma separator to separate a plasma sample from a whole blood sample; actuating a detection unit to obtain first data indicative of a first spectrophotometer measurement of the plasma sample; actuating a lysis device to obtain a lysed blood sample from the whole blood sample; actuating the detection unit to obtain second data indicative of a second spectrophotometer measurement of the lysed blood sample; determining a total absorbance spectrum for the whole blood sample in which the first data is adjusted by the second data to remove effects in the first spectrophotometer measurement of the plasma sample of one or more unknown extracellular interferents in the whole blood sample.

In one aspect of the present disclosure, the computerized method may comprise determining in real time the total absorbance spectrum for the whole blood sample with the removed effects of the one or more unknown extracellular interferents.

BRIEF DESCRIPTION OF THE DRAWINGS

The foregoing summary, as well as the following detailed description of the illustrative embodiments of the present application, will be better understood when read in conjunction with the appended drawings. For the purposes of illustrating the present application, there is shown in the drawings illustrative embodiments of the disclosure. It should be understood, however, that the application is not limited to the precise arrangements and instrumentalities shown. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figure 1:
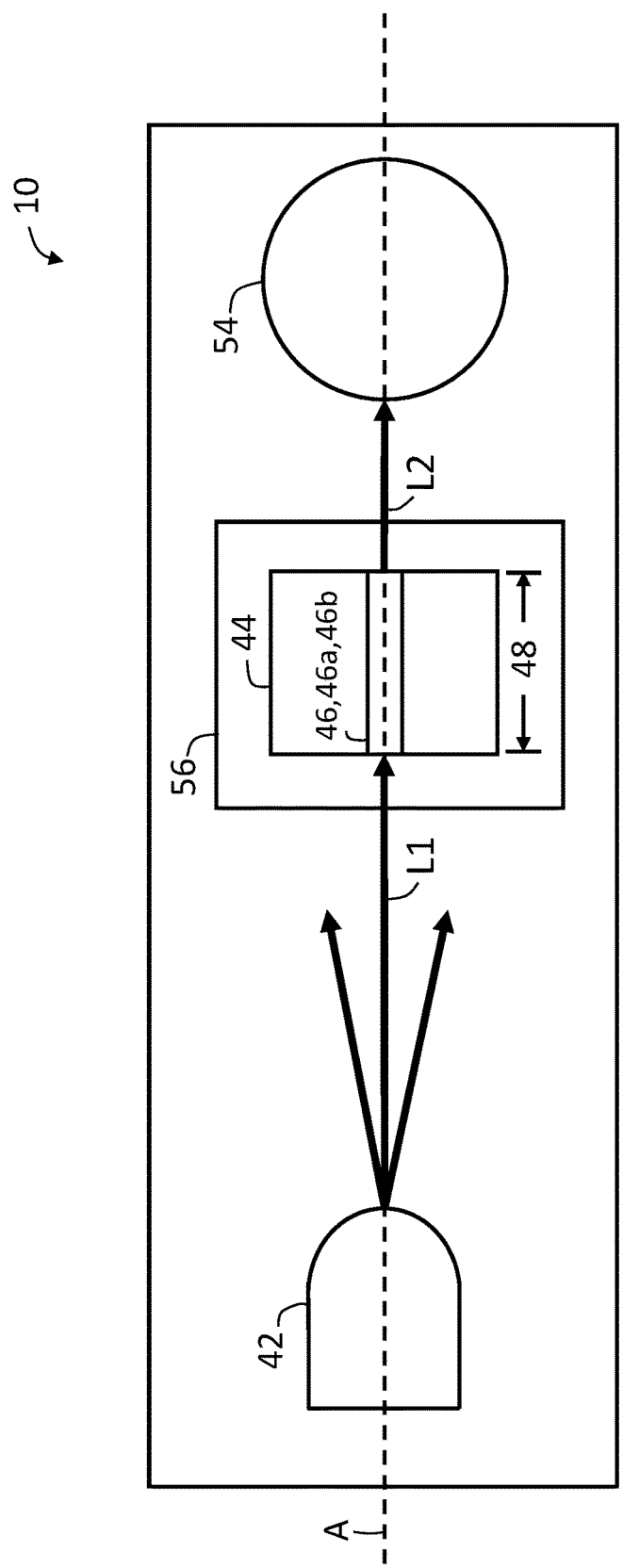
FIG. 1 is a schematic plan view of an exemplary spectrophotometer system in accordance with the present disclosure.

The present disclosure provides a sample analyzer that can make accurate determination of component concentrations without interference from unknown extracellular interferents. The sample analyzer may employ a dispensing device to pass a first portion of a blood sample into a transparent sample vessel at a first instance of time, employ a plasma separator to separate plasma from the blood sample, employ the dispensing device to pass a portion of the plasma of the blood sample into the transparent sample vessel at a second instance of time, obtain first data generated by a detector indicative of an optical signal passing through the first portion of the blood sample, and second data generated by the detector indicative of the optical signal passing through the portion of the plasma of the blood sample, the logic causing the processor to calculate a total absorbance spectrum in which the first data is adjusted by the second data. Because the first data and the second data both contain information indicative of the unknown extracellular interferent, the information with respect to the unknown extracellular interferent cancels out and is effectively removed from the total absorbance spectrum. In some embodiments, the analyzer may employ a lysis device to lyse red blood cells in the blood sample, after employing the dispensing device to pass a first portion of the blood sample into a transparent sample vessel at a first instance of time, to produce a lysed portion. The lysed portion may be used to measure forms of hemoglobin and bilirubin with the detector.

Before explaining at least one embodiment of the present disclosure in detail, it is to be understood that embodiments of the present disclosure are not limited in their application to the details of construction and the arrangement of the components or steps or methodologies set forth in the following description or illustrated in the drawings. The inventive concepts in the present disclosure are capable of other embodiments or of being practiced or carried out in various ways. Also, it is to be understood that the phraseology and terminology employed herein is for the purpose of description and should not be regarded as limiting.

In this detailed description of embodiments of the inventive concepts, numerous specific details are set forth in order to provide a more thorough understanding of the inventive concepts. However, it will be apparent to one of ordinary skill in the art that the inventive concepts disclosed and claimed herein may be practiced without these specific details. In other instances, well-known features have not been described in detail to avoid unnecessarily complicating the instant disclosure.

As used herein, language such as "including," "comprising," "having," "containing," or "involving," and variations thereof, is intended to be broad and encompass the subject matter listed thereafter, equivalents, and additional subject matter not recited or inherently present therein.

As used herein, the terms "first", "second" and the like are used to specifically identify items and are not intended, by themselves, to imply any particular order.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Throughout this disclosure and the claims, the terms "about," "approximately," and "substantially" are intended to signify that the item being qualified is not limited to the exact value specified, but includes slight variations or deviations therefrom, caused by measuring error, manufacturing tolerances, stress exerted on various parts, wear and tear, or combinations thereof, for example.

The use of the term "at least one" will be understood to include one and any quantity more than one, including but not limited to each of, 2, 3, 4, 5, 10, 15, 20, 30, 40, 50, 100, and all integers therebetween. The term "at least one" may extend up to 100 or 1000 or more, depending on the term to which it is attached; in addition, the quantities of 100/1000 are not to be considered limiting, as higher limits may also produce satisfactory results. Singular terms shall include pluralities and plural terms shall include the singular unless indicated otherwise.

The term "or combinations thereof" as used herein refers to all permutations and/or combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

In accordance with the present disclosure, certain components of the sample analysis system include circuitry. Circuitry, as used herein, could be analog and/or digital components, or one or more suitably programmed microprocessors and associated hardware and software, or hardwired logic. Also, certain portions of the implementations may be described as "circuitry" that perform one or more functions. The term "circuitry," may include hardware, such as a processor, an application specific integrated circuit (ASIC), or a field programmable gate array (FPGA), or a combination of hardware and software. Software includes one or more computer executable instructions that when executed by one or more component causes hardware to perform a specified function. It should be understood that the algorithms described herein are stored on one or more non-transitory memory. Exemplary non-transitory memory includes random access memory, read only memory, flash memory or the like. Such non-transitory memory can be electrically based or optically based.

Finally, as used herein any reference to "one embodiment" or "an embodiment" means that a particular element, feature, structure, or characteristic described in the embodiment is included in at least one embodiment. The appearances of the phrase "in one embodiment" in various places in the specification are not necessarily referring to the same embodiment, although the inventive concepts disclosed herein are intended to encompass all combinations and permutations including one or more features of the embodiments described.

Referring now to the drawings, and in particular to FIG. 1, a spectrophotometer system 10 is shown. In one embodiment, the spectrophotometer system 10 may comprise one or more light source 42, a sample vessel 44 configured to hold a specimen sample 46, and a detector 54. The one or more light source 42 may emit light L1 into the sample 46 in the sample vessel 44 and the detector 54 may detect the luminescence L2 that exits the sample vessel 44 (that is, the luminescence L2 of the sample 46). The sample vessel 44 may have a thickness which may be the path length 48 the light travels through the sample vessel 44.

In one embodiment, the detector 54 may be a spectrophotometer as is known in the art. The detector 54 may be referred to as the spectrophotometer 54 herein.

The sample vessel 44 may be configured to hold the sample 46 for analysis. The sample 46 may be any type of specimen, such as any type of liquid. For example, the sample 46 can be a biological sample or body fluid, such as blood, plasma, urine, or other fluids obtained from a patient. Furthermore, the sample 46 may also include non-biological sample liquids. The sample 46 is not limited strictly to liquids obtained from the patient. The following description describes the analysis of a whole blood sample 46, a plasma sample 46a from the whole blood sample 46, and a lysed blood sample 46b from the whole blood sample 46. However, it will be understood that other sample types may be used.

The one or more light source 42 is configured to emit the light L1 as one or more light signal along one or more axis A. The one or more light source 42 may be a light emitting diode and/or a neon lamp. In one example, the one or more light source 42 is adapted to emit an optical signal including light L1 of specified wavelength into the sample 46 contained in the sample vessel 44. For instance, the one or more light source 42 may have a light signal with a broadband white light 450 nm to 680 nm.

In some embodiments for oximetry absorbance spectra measurement, for example, for analysis of blood O2Hb, HHb, COHb, MetHb, SulfHb, Fetal Hb and Bilirubin, the one or more light source 42 may be a broadband white light source of approximately 450 nm to 680 nm to illuminate the lysed blood sample 46b and the plasma sample 46a, at separate instances of time, for the spectrophotometer 54 to perform the absorbance measurements. While halogen lamps have typically been used to serve this purpose in the past, white light emitting diodes (LED) have been employed more recently. The one or more light source 42 may produce contiguous radiation across the spectrum because many wavelengths are used. In addition to this, a precision spectral line light source may be used to calibrate the spectrophotometer 54. A neon gas lamp may be used to produce a number of precision spectral lines (one of the lines at 585.2488 nm is particularly useful in the midrange of the total spectrum), and to produce strong intensity relative to the many other lines, allowing shorter integration times to be used. In one embodiment, the neon line calibration light source may be turned on and off to periodically calibrate the spectrophotometer 54 before a measurement is made, which improves measurement precision.

In one embodiment, the spectrophotometer system 10 may include a sample vessel holder 56 that is configured to hold the sample vessel 44. The sample vessel holder 56 may be located adjacent to the detector 54 on the optical axis A. However, the sample vessel holder 56 and detector 54 may be arranged in configurations other than those specifically shown in the drawings.

In one embodiment, the spectrophotometer system 10 may include one or more of the following: a reflector, a lens, a filter, a light sensor (to monitor the intensity of the light L1), and/or a polarizer.

Figure 2:
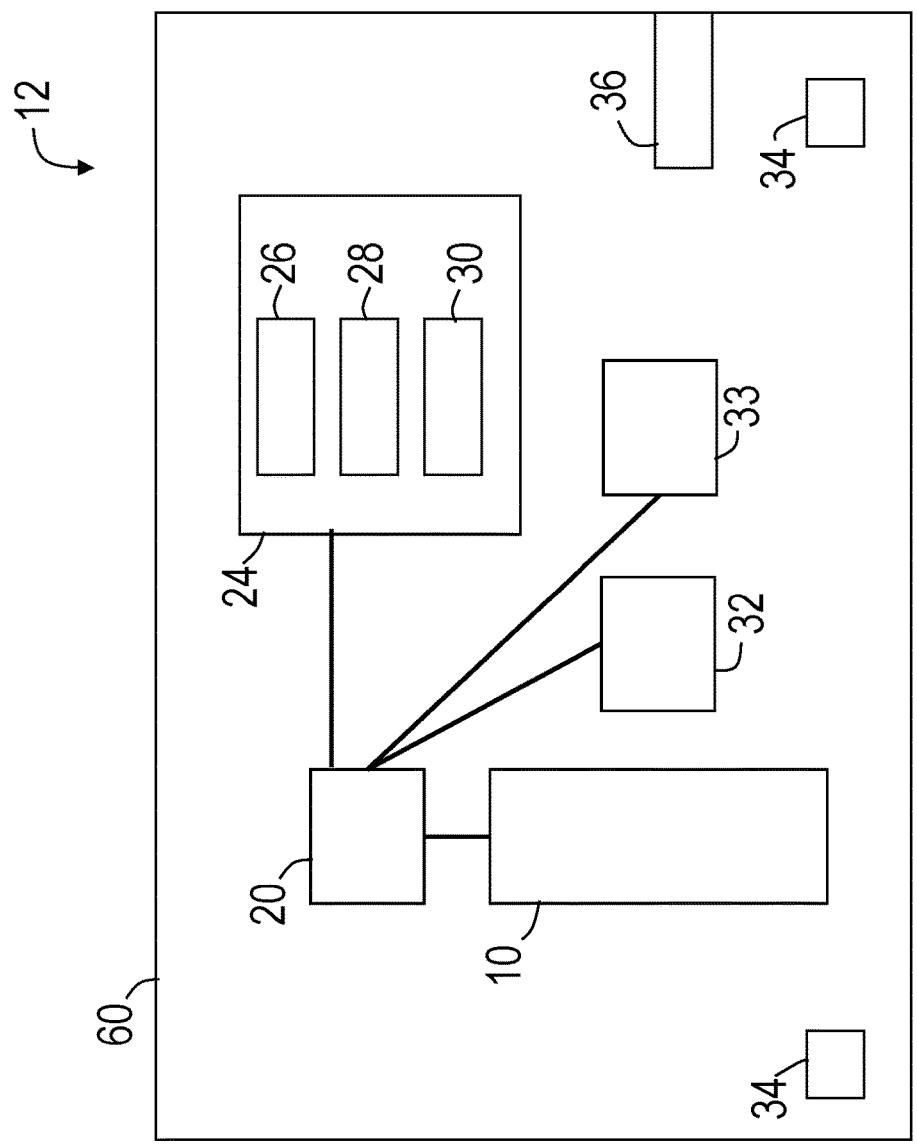
FIG. 2 is a schematic plan view of a sample analyzer according to an embodiment of the present disclosure.

In one embodiment, as shown in FIG. 2, the spectrophotometer system 10 may be part of a sample analyzer 12. The sample analyzer 12 may have a housing 60 having an internal space, and one or more components of the sample analyzer 12 may be positioned on or in the housing.

In one embodiment, the sample analyzer 12 may include a controller 20 that controls operation of the spectrophotometer system 10. The sample analyzer 12 may comprise a dispensing device 24 to dispense the sample(s) 46 from one or more sample vial, and/or reagent, into the sample vessel 44. The dispensing device 24 may include a motor 26 that powers the dispensing device 24, a pump 28, and a valve 30, such as a lee valve. The controller 20 may also control the motor 26 that powers the dispensing device 24, the pump 28 and the valve 30. The pump 28 may provide a plurality of liquids into the sample vessel 44, such as a wash solution, a clear blank calibration (CAL) solution, and one or more portions of the sample 46.

For example, when the sample 46 is blood, the controller 20 may actuate the pump 28 to provide the wash solution into the sample vessel 44 to clean the sample vessel 44, followed by distinct portions of the blood sample 46. The distinct portions may include plasma as the plasma sample 46a, whole blood as the whole blood sample 46, or lysed blood as the lysed blood sample 46b. The controller 20 may actuate the pump 28 to clean the sample vessel 44 with the wash solution in between the distinct portions of the blood being provided by the pump 28 into the sample vessel 44. In some embodiments, the sample analyzer 12 may include more than one pump 28 with each pump supplying a particular type of solution into the sample vessel 44.

In certain embodiments, such as for sample analyzers adapted to analyze blood and/or plasma samples, the sample analyzer 12 may further comprise a plasma separator 32 to separate plasma from the blood sample 46 for analysis. In some embodiments, the sample analyzer 12 may further comprise a lysis device 33 for lysing red blood cells in the blood sample 46. The plasma separator 32 may utilize active or passive methods to separate a portion of the plasma from the whole blood, prior to lysing red blood cells in the blood sample 46. Exemplary active methods include magnetic, dielectrophoretic, centrifugal, or acoustic separation methods. In this case, the plasma separator 32 would be constructed based upon the requirements of at least one of the active methods. For example, to utilize acoustic separation methods, the plasma separator 32 may include a piezoelectric element connected to a glass slide supporting the blood sample, and a driver that provides an electric signal to the piezoelectric element with a sufficient frequency and voltage to separate the red blood cells from the plasma, without lysing or otherwise damaging the red blood cells. In this case, the plasma can be directed to a predetermined location on the glass slide so that an absorption reading of the plasma (substantially devoid of red blood cells) can be taken while the plasma separator 32 is actuated to actively separate the red blood cells from the plasma. Exemplary passive methods include hydrodynamic, sedimentation, and filtration methods. In one embodiment, the lysis device 33 and the plasma separator 32 may be a single device. In one embodiment, the lysis device 33 may include a piezoelectric element connected to a glass slide supporting the blood sample, and a driver that provides an electric signal to the piezoelectric element with a sufficient frequency and voltage for lysing the red blood cells.

In one embodiment, the lysis device 33 and/or the plasma separator 32 may be configured as described in the provisional application entitled "ACOUSTOPHORETIC LYSIS DEVICES AND METHODS", application Ser. No. 63/036,537, filed on Apr. 28, 2020, which is hereby incorporated in its entirety herein.

In one embodiment, the sample analyzer 12 may further comprise one or more position sensors 34 used to determine the position of the stage 16 and/or spectrophotometer system 10 with respect to the dispensing device 24. A vacuum port 36 may be included to control pressure in the housing 14.

The sample vessel 44 and/or the spectrophotometer system 10 may be stationary or movable so as to bring the sample 46 and/or portions of the sample 46 into the path of an optical signal used by the spectrophotometer system 10 to obtain a transmittance reading of the sample 46 and/or portion thereof.

It should also be appreciated that the sample analyzer 12 can be adapted to analyze multiple samples 46. In one example, the sample analyzer 12 may include a cartridge adapted to hold a plurality of sample vessels 44. In yet another example, the sample analyzer 12 may be an automated analyzer that includes a moveable carousel for holding multiple sample vessels 44. Such an analyzer may include multiple detectors 54 testing for different analytes of interest. An exemplary automated analyzer is disclosed in U.S. Patent App. Pub. No. 2010/0150779, incorporated herein by reference in its entirety. Other exemplary sample analyzers include the ADVIA® and DIMENSION® analyzers produced by Siemens Healthcare Diagnostics Inc.

The controller 20 may include circuitry configured to embody and/or execute the logic of the processes described herein. Logic embodied in the form of software instructions and/or firmware may be executed on a dedicated computer system or computer systems, on distributed processing computer systems, and/or the like. In some embodiments, the logic may be implemented in a stand-alone environment operating on a single computer system and/or logic may be implemented in a networked environment such as a distributed computer system using multiple computers and/or processors. For example, one or more microprocessors may work together or independently to execute processor executable code using one or more memories.

The spectrophotometer system 10 incorporated with the sample analyzer 12 illustrated in FIGS. 1 and 2 represent an exemplary sample analyzer that illustrates inventive concepts set forth in the present disclosure. However, the sample analyzer 12 as described herein can be configured in other manners adapted to make measurements of the sample 46 illuminated in the sample vessel 44. In one embodiment, the sample analyzer may be configured as a "RAPIDPoint 405" analyzer or a "RAPIDPoint 500" analyzer, both manufactured by Siemens Medical Solutions, Malvern, Pa.

Figure 3:
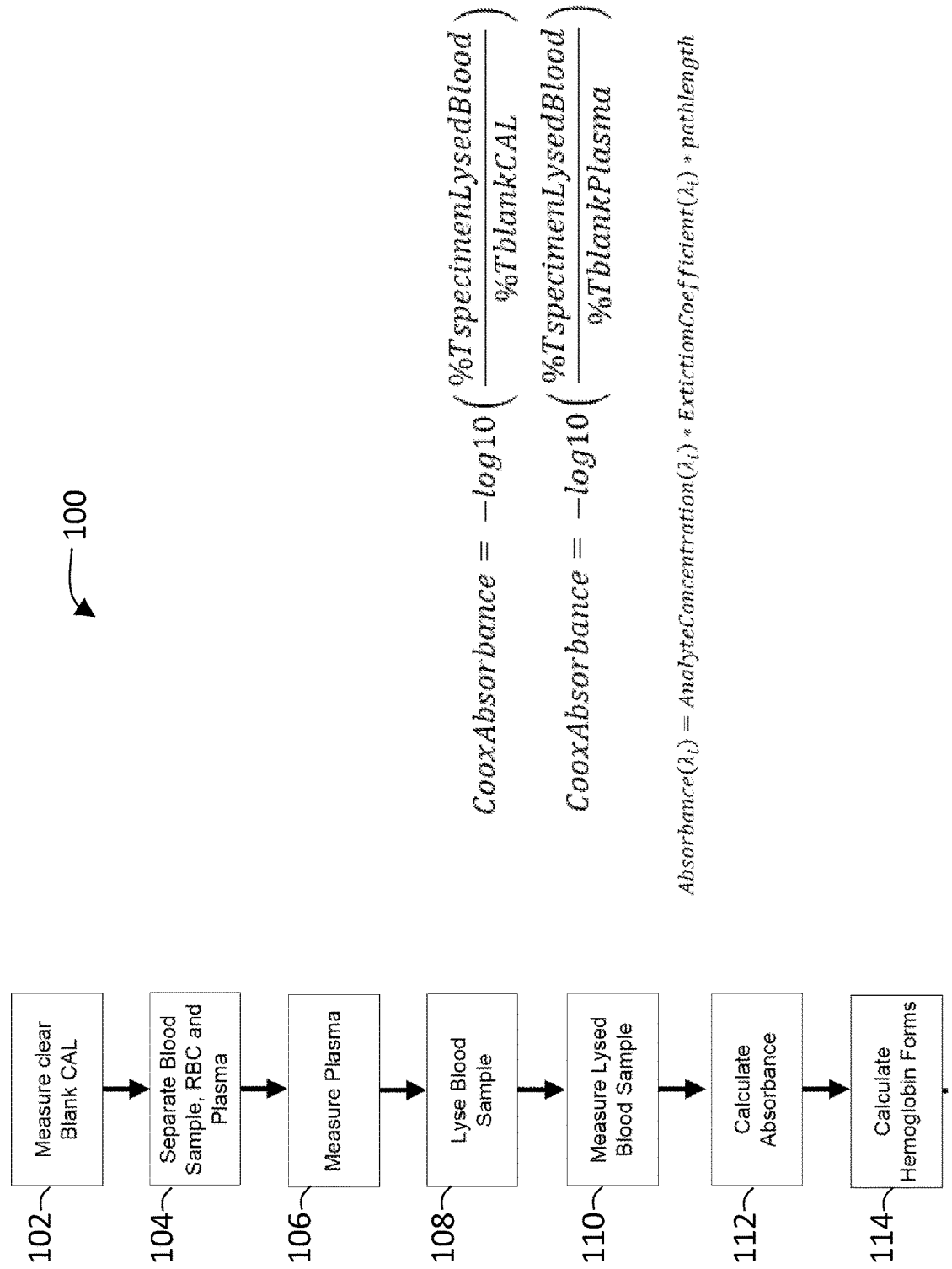
FIG. 3 is a flow chart of an exemplary method in accordance with the present disclosure.

Referring now to FIG. 3, a flow chart of an exemplary method 100 of use of the sample analyzer 12 to determine a Coox absorbance measurement in blood samples in accordance with the present disclosure is disclosed. To address the role of the unknown interferent(s) in the detection of the presence and amount of the principal forms of hemoglobin, the present disclosure adjusts the transmittance measurement of the whole blood sample 46 and/or the lysed blood sample 46b with the transmittance measurement of the plasma sample 46a to reduce any interference in the measurement of the principal forms of hemoglobin caused by the unknown interferent(s). This adjustment can be made without having an extinction coefficient stored in the non-transitory memory of the controller 20 (or even accessed by a processor of the controller 20) and without having an extinction coefficient associated with the specific spectral signature of the unknown interferent. Rather than mathematically applying a known extinction coefficient for each hemoglobin form or other analyte of interest to the total Coox Absorbance measurement to determine a concentration for each hemoglobin form (or other analyte of interest) from the total absorbance measurement, as done in the prior art, the current method measures in real time the absorbance measurement without the unknown interferent(s).

In one embodiment, the controller 20 may be actuated to obtain an absorbance measurement for specific forms of hemoglobin. The controller 20 may actuate the pump 28 to wash the transparent sample vessel 44. A clear blank CAL solution may be delivered into the vessel 44. Then, the controller 20 may actuate the spectrophotometer system 10 to measure the transmittance of the CAL solution in step 102, as further explained below.

In one embodiment, the controller 20 may actuate the spectrophotometer system 10 to measure the transmittance of the whole blood sample 46.

Next, the controller 20 may actuate the plasma separator 32 to separate the plasma 46a from the whole blood sample 46, as indicated by a step 104, to generate the plasma sample 46a. In step 106, the controller 20 may actuate the spectrophotometer system 10 to measure the transmittance of the plasma sample 46a.

In one embodiment, the controller 20 may actuate the lysis device 33 to lyse at least a portion of the whole blood sample 46 at a step 108. The controller 20 may actuate the pump 28 to place a portion of the lysed blood sample 46b of the lysed blood within the sample vessel 44, and measure the transmittance of the lysed blood sample 46b at step 110.

The order of measuring the transmittance of the whole blood sample 46, the plasma sample 46a, and the lysed blood sample 46b may vary. When a single transparent sample vessel 44 is used, the controller 20 may actuate the pump 28 to wash the transparent sample vessel 44 between new samples being applied into the transparent sample vessel 44.

Once the transmittance of the plasma sample 46a and the transmittance of the whole blood sample 46 and/or the lysed blood sample 46b has been measured, the controller 20 may calculate a total absorbance spectrum in a step 112. To calculate the total absorbance spectrum, the measurement of the whole blood sample 46 is adjusted by the measurement of the plasma sample 46a using EQUATION 1, explained below, for example. The controller 20 can then calculate the presence and amount of the specific hemoglobin forms in a step 114 utilizing the lysed blood sample 46b by using EQUATION 2, explained below, for example.

The method 100 can be automated as a sequence of instructions that are performed for determining unknown interferent(s) in the sample 46, and such sequence can be repeated for conducting readings on a plurality of samples 46.

In one embodiment, the detection of unknown interferent(s) and/or the adjustment may be displayed to a user on a display.

Now, the algorithms that may be used in the method 100 will be discussed.

Absorption spectroscopy uses data pretreatment by converting the measured sample transmittance into sample absorption, as is well known in the art. The logarithmic relationship of conventional sample absorption to sample transmittance is given by the following equations:

$$A = -\log(T)$$

and $$T = I/I_o$$

where:
A is the calculated absorption,
T is the calculated transmittance,
I is the measured intensity due to the sample, and
$I_o$ is the measured intensity with a blank sample such as deionized water.

In multivariate analysis, multiple measurements are made to permit the estimate of concentrations in the samples 46 with several components. In absorption spectroscopy measurements at multiple wavelengths of light are often used to provide the spectral information needed for an accurate analysis. Vectors and matrices are used to simplify the equations. The use of vectors in column or row format depends on the preference of the writer. In the description of this invention, vectors are assumed to be in column format and annotated with small, boldface letters. However, this notation and format does not limit the scope of the disclosure. Matrices will be denoted with capital, boldface letters.

The measured spectrum of an ideal sample can be described as:

$$A = E * c$$

where:
a is the column vector for the sample's absorption spectrum with each row element corresponding to sample absorption at a particular wavelength of light,
E is a matrix of column vectors, each representing the absorption spectrum (extinction) of a component or factor at particular wavelengths, and
c is a column vector describing the concentrations of the components and factors in E (including the scatter terms).

Figure 5:
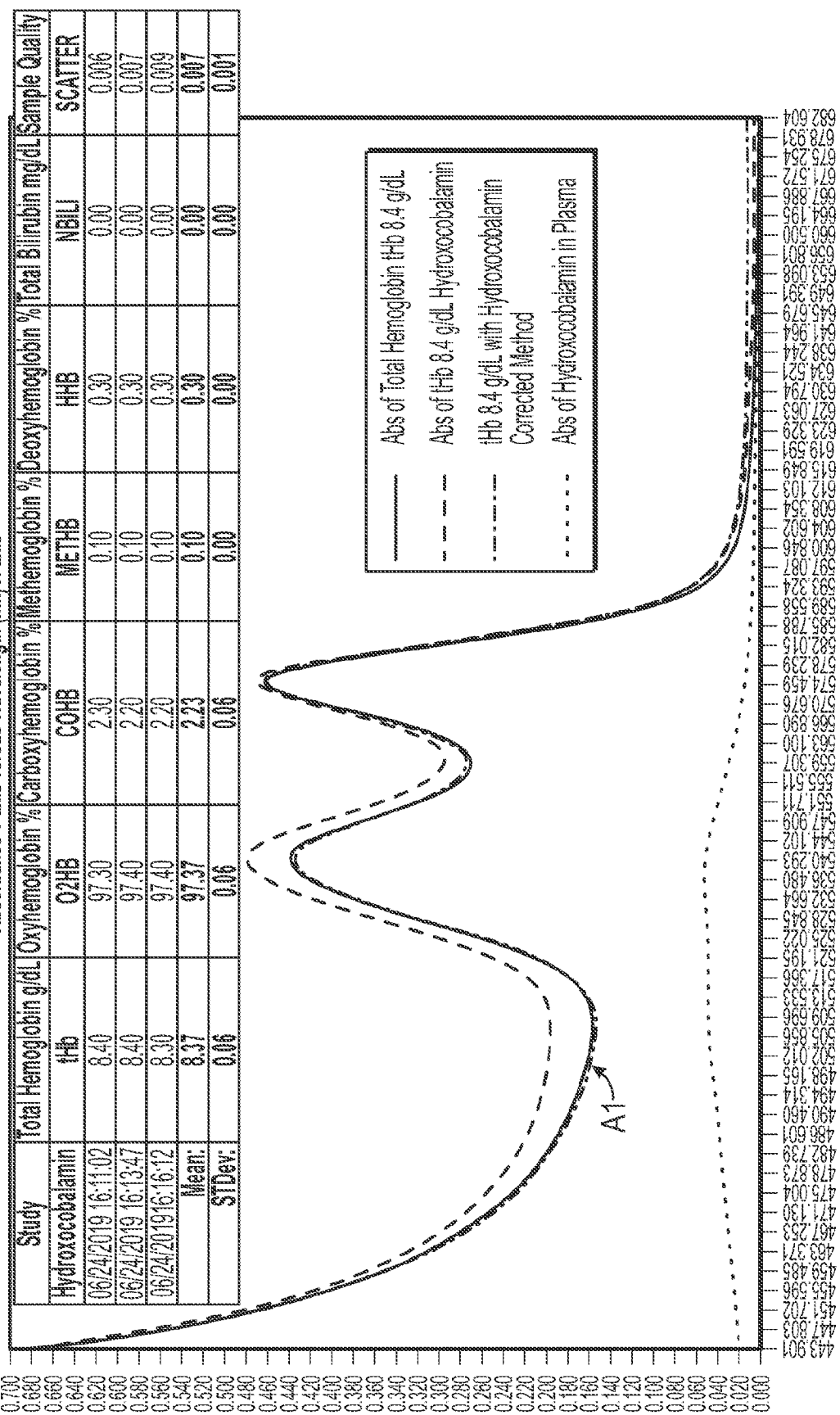
FIG. 5 is a graph of exemplary Absorbance measurements and method correction with analyte results in accordance with the present disclosure.

In an analysis of lysed and non-turbid blood for concentrations of the principal forms of hemoglobin, Oxyhemoglobin (O2Hb), Deoxyhemoglobin (HHb), Carboxyhemoglobin (COHb) and Methemoglobin (MetHb), total or neonatal Bilirubin (BILI), Cyan Methemoglobin (CN_METHb), Sulfhemoglobin (SulfHb) (intracellular interferent), Methylene blue dye (METH_BLUE) (extracellular interferent), the E matrix is formed by the eight vectors representing the eight absorption spectra (extinction coefficients) of these components as in the following equation:

$$E_{LYSED} = [e_{O2Hb} e_{HHb} e_{COHb} e_{MetHb} e_{CN\_METHb} e_{SULFHb} e_{BILI} e_{METH\_BLUE}],$$

where $e_{Hb}$ denotes the column vector for the corresponding hemoglobin. Experimental results illustrating these spectra are shown in FIG. 5.

This model of absorption is adequate for determining component concentrations in homogenous samples with low turbidity and known interferents in which each of the known interferents has an extinction coefficient.

When an unknown interferent exists within the lysed blood sample 46b, the E matrix will take on unknown absorption values due to the presence of the unknown interferent (designated in the equations by "UNKNOWN"). Unknown interferents are mainly extracellular and may result due to patients receiving new drug therapies. The unknown interferents thus occur mainly within the plasma and not within the red blood cells within the blood sample 46. Thus, the E matrix for the lysed blood sample 46b having an unknown interferent (likely due to drug therapy) will have the following form:

$$E_{LYSED} = [e_{O2Hb} e_{HHb} e_{COHb} e_{MetHb} e_{CN\_METHb} e_{SULFHb} e_{BILI} e_{METH\_BLUE} e_{UNKNOWN}]$$

And, the E matrix for the plasma sample 46a from the blood sample 46 will have the following form:

$$E_{PLASMA} = [e_{BILI} e_{METH\_BLUE} e_{BILI} e_{UNKNOWN}]$$

Thus, in accordance with the present disclosure, any unknown interferent in the $E_{LYSED}$ matrix can be removed by adjusting the $E_{LYSED}$ matrix with the $E_{PLASMA}$ matrix.

In one embodiment, unknown interference correction can be implemented ratiometrically using the following equation:

$$CooxAbsorbance = -\log 10\left(\frac{\% \ TspecimenLysedBlood}{\% \ TblankPlasma}\right) \quad \text{EQUATION 1}$$

The CooxAbsorbance is calculated using the measured percent transmission blood sample signals. The spectrophotometer 54 may measure the % TblankPlasma (that is, the percentage transmittance through the plasma sample 46a) in the denominator within the parenthesis of Equation 1 before the sample 46 is lysed by the use of plasma separation such as acoustophoresis. During plasma separation, the red blood cells are intact and move out of the field of view of the spectrophotometer 54. The transmittance through the plasma sample 46a contains all extracellular interferences.

The spectrophotometer 54 may measure the patient lysed blood sample 46b % TspecimenLysedBlood (that is, the percentage transmittance through the lysed blood sample 46b) after plasma separation and after the blood sample 46 is lysed. The lysing action breaks up the red blood cell casings releasing the heme in the cells mixing the sample thoroughly with the plasma.

A clear calibration (CAL) solution may be used in any blood sample Coox system to flush clean the blood sample vessel 44, ensuring residual substances such as carryover from a previous blood sample are removed, and the vessel 44 is optically clear prior to measuring a new patient blood sample. Additionally, the CAL solution provides a 100% transmission signal at all wavelengths, and may be used to normalize the light source signal. The second form of Equation 1, commonly used in the art of blood Co-Oximetry, substitutes the denominator term with the clear CAL, as shown in Equation 2 below:

$$CooxAbsorbance = -\log 10\left(\frac{\% \ TspecimenLysedBlood}{\% \ TblankCAL}\right) \quad \text{EQUATION 2}$$

where % TspecimenLysedBlood is the transmittance measurement for the lysed blood sample 46b, and % TblankPlasma is the transmittance measurement for the plasma sample 46a.

Then, the absorbance for a given wavelength (i) of the matrix is known from the measurement of the patient blood sample 46, the specific analyte of interest's concentration is calculated using the blood sample signal measurement by rearranging this equation to solve for the AnalyteConcentration as shown below in Equation 3:

Absorbance($\lambda_i$)=AnalyteConcentration($\lambda_i$)*ExtictionCoefficient($\lambda_i$)*pathlength         EQUATION 3:

where pathlength is the thickness of the sample vessel 44 containing the blood sample 46.

Using the above equations with the measured blood sample transmission signals, and the with the analyte extinction coefficients for Oxyhemoglobin, Deoxyhemoglobin Carboxyhemoglobin, and Methemoglobin, the analyte concentrations are calculated, the unknown interference in the blood plasma sample 46a is eliminated by the radiometric method.

FIGS. 4-7 are plots of experimental results of the method 100 of use of the sample analyzer 12 in correcting for unknown interferences in representative patient blood samples 46. For explanatory purposes, in the experimental analysis Hydroxocobalamin is used as the unknown extracellular interferant in plasma. However, it will be understood that the extracellular interferent may be any unknown interferent or interferents.

Figure 4:
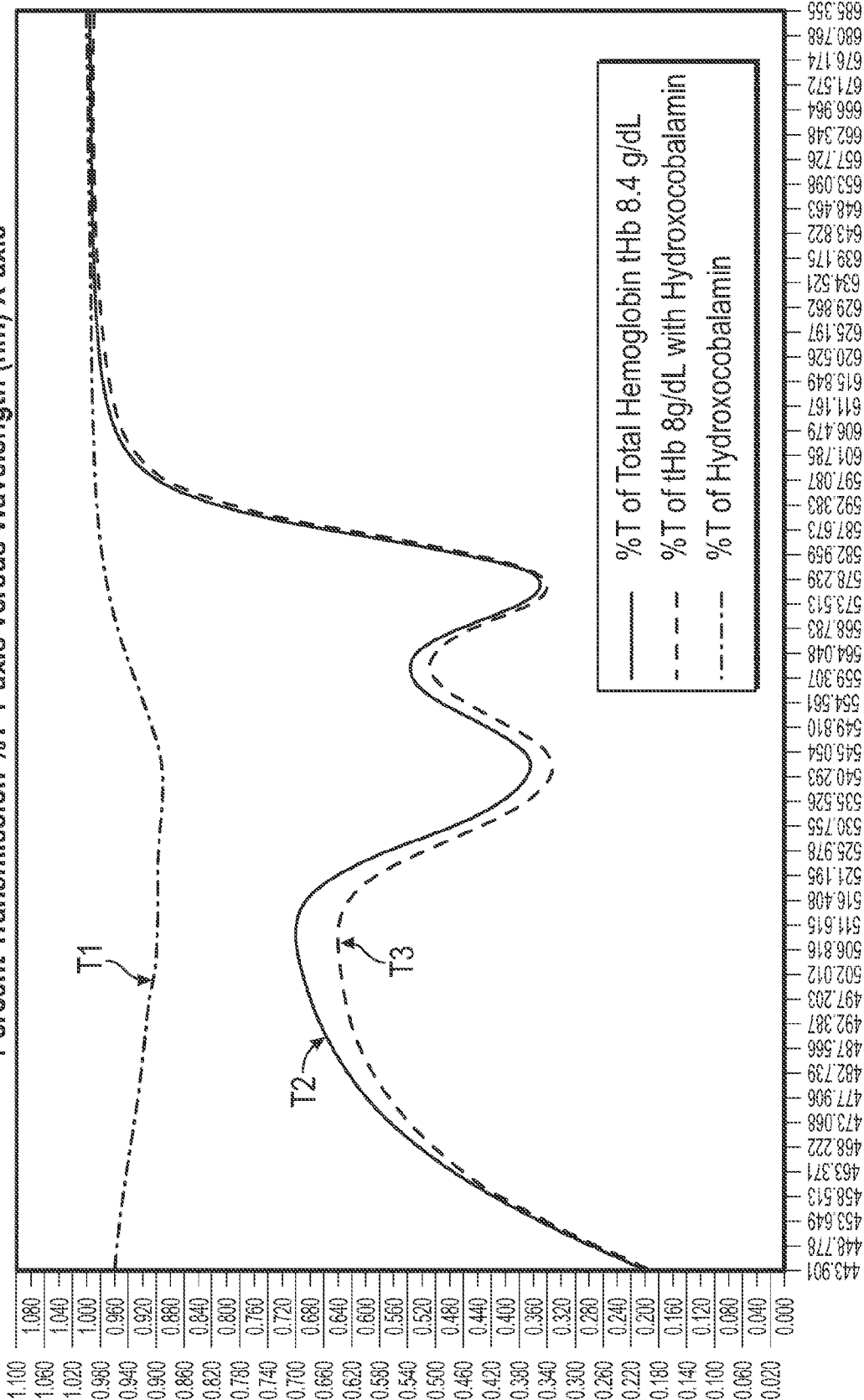
FIG. 4 is a graph of exemplary Transmission (% T) normalized spectrophotometer measurements in accordance with the present disclosure.

FIG. 4 illustrates experimental normalized spectrophotometer measurements of percent transmission (y-axis) versus wavelength (x-axis) of a blood sample 46 and a plasma sample 46a. The first curve (T1) is a measured spectral profile of transmittance of hydroxocobalamin (B12) in the plasma sample 46a as determined by the analyzer 12. The third curve (T3) is a measured spectral profile of transmittance of hemoglobin with the hydroxocobalamin in the blood sample 46 as determined by the analyzer 12. The second curve (T2) is a measured spectral profile of transmittance of hemoglobin without the hydroxocobalamin in the blood sample 46 as determined by the analyzer 12 having removed the unknown interferent. The analyzer 12 corrects for the presence of hydroxocobalamin (B12) in the blood sample 46 to measure the spectral profile of transmittance of hemoglobin in the blood sample 46, which produces the curve T2.

FIG. 5 illustrates experimental Absorbance measurements (y-axis) versus wavelength (x-axis), showing method correction with analyte results. The chart in FIG. 5 illustrates experimental measurements from the analyzer 12 in the absorbance domain. The line A1 is the corrected absorbance result for the blood sample 46, that is, the absorbance result without the unknown interferent.

Figure 6:
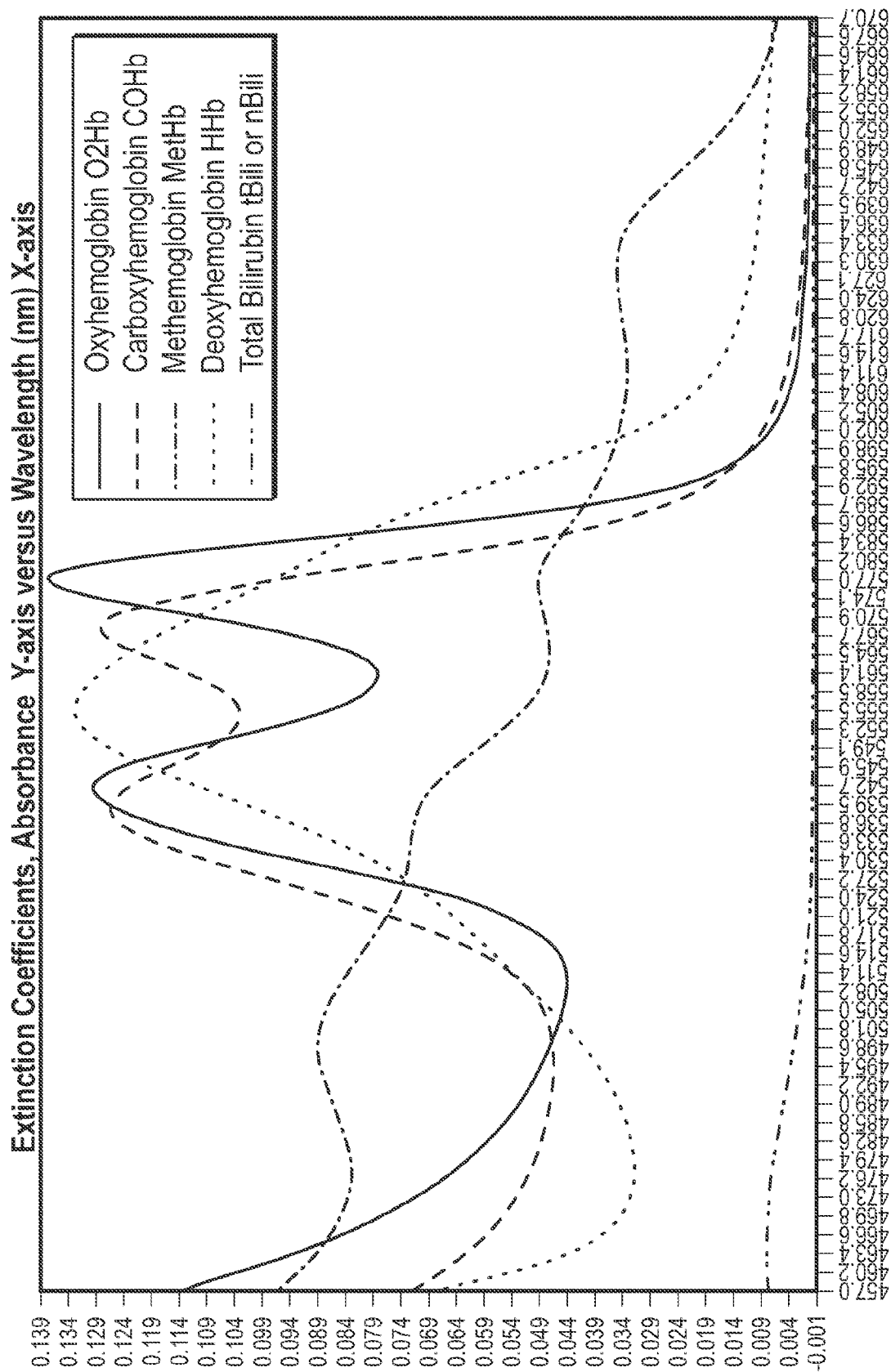
FIG. 6 is a graph of exemplary Extinction coefficients in accordance with the present disclosure.

FIG. 6 illustrates experimental extinction coefficients for multiple interferents, absorbance measurements from the analyzer 12, showing percent transmission (y-axis) versus wavelength (x-axis). The extinction coefficients are reference spectra that show the absorbance of a sample having 100% of the particular interferent. In one embodiment, the analyzer 12 may check the sample 46 against known interferents, using the known interference extinction coefficients, before determining the unknown interferent(s). In one embodiment, the analyzer 12 may check the sample 46 against other known interferents (not shown) using the known interference extinction coefficients before determining the unknown interferent(s).

It should be understood that other manners to correct the transmittance of the lysed blood sample 46b with the plasma sample 46a can be used, such as preparing the blood sample 46 before introducing it to the sample analyzer 12. Preparing the blood sample 46 may involve precisely splitting the sample 46 into two aliquots, one that is centrifuged to harvest only the plasma sample 46a, and a second that is the original sample 46 to then be lysed into the lysed blood sample 46b. However, splitting the blood sample 46 may require a larger sample volume, specialized laboratory equipment, a skilled operator, approved protocols, and is time consuming, also reducing the accuracy of the measurements.

The sample analyzer 12 described in the present disclosure is capable of exploitation in industry in accordance with how it can be made and/or used.

Those skilled in the art will also appreciate that the present disclosure may be applied to other applications and may be modified without departing from the scope of the present disclosure. Accordingly, the scope of the present disclosure is not intended to be limited to the exemplary embodiments described above, but only by the appended claims.

The invention claimed is:

1. A blood analyzer, comprising:
a housing assembly that defines an internal space;
a light source mounted to the housing assembly in the internal space, the light source configured to generate an optical signal having wavelengths spanning a range from 450 nm to 680 nm, the optical signal being transmitted through a path;
a detector within the path of the optical signal, the detector configured to generate data indicative of intensity of the optical signal at wavelengths within the range;
a transparent sample vessel positioned within the path between the light source and the detector such that the optical signal passes through the transparent sample vessel prior to being received by the detector;
a plasma separator to separate plasma from a blood sample to create a plasma sample;
a dispenser adapted to pass a first portion of the blood sample into the transparent sample vessel at a first instance of time, the first portion being whole blood or lysed blood, and to pass the plasma sample into the transparent sample vessel at a second instance of time; and
a controller having a processor executing logic that when executed by the processor causes the processor to obtain first data generated by the detector indicative of the optical signal passing through the first portion of the blood sample, and second data generated by the detector indicative of the optical signal passing through the plasma sample, the logic causing the processor to calculate a total absorbance spectrum in which the first data is adjusted by the second data to remove effects of one or more unknown extracellular interferents in the blood sample.

2. The blood analyzer of claim 1, wherein the first data has first values indicative of absorbance of the first portion of the blood sample at various wavelengths, and the second data has second values indicative of absorbance of the plasma sample at various wavelengths, and wherein the first data is divided by the second data.

3. The blood analyzer of claim 1, further comprising an acoustophoretic lysis device and wherein the first portion of the blood sample is lysed with the acoustophoretic lysis device.

4. The blood analyzer of claim 3, wherein the acoustophoretic lysis device comprises a piezoelectric element connected to a glass slide supporting the blood sample, and a driver that provides an electric signal to the piezoelectric element with a sufficient frequency and voltage for lysing the first portion of the blood sample.

5. The blood analyzer of claim 1, wherein the plasma separator further is configured to lyse the first portion of the blood sample.

6. The blood analyzer of claim 1, wherein the plasma separator comprises a piezoelectric element connected to a glass slide supporting the blood sample, and a driver that provides an electric signal to the piezoelectric element with a sufficient frequency and voltage to separate plasma in the blood sample.

7. A computerized method performed by a processor executing computer executable code stored on a computer readable medium, comprising:

actuating a plasma separator to separate a plasma sample from a whole blood sample;
actuating a detector to obtain first data indicative of a first spectrophotometer measurement of the plasma sample;
actuating the detector to obtain second data indicative of a second spectrophotometer measurement of a lysed blood sample obtained from the whole blood sample; and
determining a total absorbance spectrum for the whole blood sample in which the first data is adjusted by the second data to remove effects in the first spectrophotometer measurement of the plasma sample of one or more unknown extracellular interferents in the whole blood sample.

8. The computerized method of claim 7, further comprising determining in real time the total absorbance spectrum for the whole blood sample with the removed effects of the one or more unknown extracellular interferents.

9. The computerized method of claim 7, wherein the plasma separator comprises a piezoelectric element connected to a glass slide supporting the blood sample, and a driver that provides an electric signal to the piezoelectric element with a sufficient frequency and voltage to separate plasma in the blood sample.

10. The computerized method of claim 7, further comprising actuating an acoustophoretic lysis device to obtain a lysed blood sample from the whole blood sample wherein the acoustophoretic lysis device comprises a piezoelectric element connected to a glass slide supporting the blood sample, and a driver that provides an electric signal to the piezoelectric element with a sufficient frequency and voltage for lysing a first portion of the blood sample.

11. The computerized method of claim 10, wherein the plasma separator and the acoustophoretic lysis device are combined.

12. A blood analyzer, comprising:
a detector within a path of an optical signal from a light source, the detector configured to generate data indicative of intensity of the optical signal at wavelengths within a range from 450 nm to 680 nm;
a transparent sample vessel positioned within the path between the light source and the detector such that the optical signal passes through the transparent sample vessel prior to being received by the detector;
a plasma separator to separate plasma from a blood sample to create a plasma sample;
a dispenser adapted to pass a first portion of the blood sample into the transparent sample vessel at a first instance of time, the first portion being whole blood or lysed blood, and to pass the plasma sample into the transparent sample vessel at a second instance of time; and
a controller having a processor executing logic that when executed by the processor causes the processor to obtain first data generated by the detector indicative of the optical signal passing through the first portion of the blood sample, and second data generated by the detector indicative of the optical signal passing through the plasma sample, the logic causing the processor to calculate a total absorbance spectrum in which the first data is adjusted by the second data to remove effects of one or more unknown extracellular interferents in the blood sample.

13. The blood analyzer of claim 12, wherein the first data has first values indicative of absorbance of the first portion of the blood sample at various wavelengths, and the second data has second values indicative of absorbance of the plasma sample at various wavelengths, and wherein the first data is divided by the second data.

14. The blood analyzer of claim 12, further comprising an acoustophoretic lysis device and wherein the first portion of the blood sample is lysed with the acoustophoretic lysis device.

15. The blood analyzer of claim 14, wherein the acoustophoretic lysis device comprises a piezoelectric element connected to a glass slide supporting the blood sample, and a driver that provides an electric signal to the piezoelectric element with a frequency and voltage for lysing the first portion of the blood sample.

16. The blood analyzer of claim 12, wherein the plasma separator comprises a piezoelectric element connected to a glass slide supporting the blood sample, and a driver that provides an electric signal to the piezoelectric element with a frequency and voltage to separate plasma in the blood sample.

17. The blood analyzer of claim 16, wherein the electrical signal is a first electrical signal and wherein the plasma separator is further adapted such that the driver provides a second electric signal to the piezoelectric element with a frequency and voltage for lysing the first portion of the blood sample.

* * * * *